US009029775B2

(12) United States Patent
Demers et al.

(10) Patent No.: US 9,029,775 B2
(45) Date of Patent: May 12, 2015

(54) TERAHERTZ FREQUENCY DOMAIN SPECTROMETER WITH PHASE MODULATION OF SOURCE LASER BEAM

(75) Inventors: Joseph R. Demers, North Hollywood, CA (US); Ronald T. Logan, Jr., Pasadena, CA (US)

(73) Assignee: Joseph R. Demers, Pasadena, CA (US)

( * ) Notice: Subject to any disclaimer, the term of this patent is extended or adjusted under 35 U.S.C. 154(b) by 467 days.

(21) Appl. No.: 13/565,021

(22) Filed: Aug. 2, 2012

(65) Prior Publication Data

US 2012/0326039 A1    Dec. 27, 2012

Related U.S. Application Data

(63) Continuation-in-part of application No. 12/861,651, filed on Aug. 23, 2010, now Pat. No. 8,604,433, which is a continuation-in-part of application No. 12/465,219, filed on May 13, 2009, now Pat. No. 7,781,736.

(60) Provisional application No. 61/054,344, filed on May 19, 2008.

(51) Int. Cl.
*G01N 21/35* (2014.01)
*G01J 3/10* (2006.01)
(Continued)

(52) U.S. Cl.
CPC .............. *G01J 3/10* (2013.01); *G01N 21/3586* (2013.01); *G01J 3/42* (2013.01); *G01J 3/4531* (2013.01); *G01N 21/3581* (2013.01); *G01N 21/39* (2013.01)

(58) Field of Classification Search
CPC ................... G01N 21/3581; G01N 21/3586
USPC ......................... 250/338.07, 338.08
See application file for complete search history.

(56) References Cited

U.S. PATENT DOCUMENTS

| 4,594,511 A | 6/1986 | Cooper et al. |
| 5,379,110 A | 1/1995 | Matsui et al. |

(Continued)

FOREIGN PATENT DOCUMENTS

| EP | 1233527 | 8/2002 |
| GB | 2381121 | 4/2003 |

(Continued)

OTHER PUBLICATIONS

Brown, "Advancements in Photomixing and Photoconductive Switching for THz Spectroscopy and Imaging," *Proc. of SPIE*, 2013; 7938:793802-1-793802-16. U.S. Appl. No. 61/054,344, filed May 19, 2008, Logan, Jr. et al.
Brown et al., "Characterization of a Planar Self-Complementary Square-Spiral Antenna in the THz Region," *Microwave and Optical Technology Letters*, Mar. 2006; 48(3):524-529.

(Continued)

*Primary Examiner* — Casey Bryant
(74) *Attorney, Agent, or Firm* — Pritzkau Patent Group, LLC

(57) ABSTRACT

An apparatus for analyzing, identifying or imaging an target including first and second laser beams coupled to a pair of photoconductive switches to produce CW signals in one or more bands in a range of frequencies greater than 100 GHz focused on, and transmitted through or reflected from the target; and a detector for acquiring spectral information from signals received from the target and using a multi-spectral heterodyne process to generate an electrical signal representative of some characteristics of the target. The lasers are tuned to different frequencies and a phase modulator in the path of one laser beam allows the constructive or destructive interference of the signals on the detector as the laser beams are swept in frequency to be adjusted to achieve greater resolution in one or more selected frequency bands.

17 Claims, 3 Drawing Sheets

(51) Int. Cl.
*G01J 3/42* (2006.01)
*G01J 3/453* (2006.01)
*G01N 21/3581* (2014.01)
*G01N 21/39* (2006.01)
*G01N 21/3586* (2014.01)

(56) References Cited

U.S. PATENT DOCUMENTS

| | | | |
|---|---|---|---|
| 5,379,309 A | 1/1995 | Logan, Jr. | |
| 5,623,145 A | 4/1997 | Nuss | |
| 6,304,219 B1 | 10/2001 | Rothe et al. | |
| 6,348,683 B1 | 2/2002 | Verghese et al. | |
| 6,434,496 B1 | 8/2002 | Dong et al. | |
| 6,545,785 B1 | 4/2003 | Heflinger et al. | |
| 6,811,552 B2 | 11/2004 | Weil, Sr. et al. | |
| 6,816,647 B1 | 11/2004 | Rudd et al. | |
| 6,828,558 B1 | 12/2004 | Arnone et al. | |
| 6,844,552 B2 * | 1/2005 | Zhang et al. | 250/338.1 |
| 6,849,852 B2 | 2/2005 | Williamson | |
| 6,865,014 B2 | 3/2005 | Ciesla et al. | |
| 6,957,099 B1 | 10/2005 | Arnone et al. | |
| 7,126,078 B2 | 10/2006 | Demers et al. | |
| 7,174,037 B2 | 2/2007 | Arnone et al. | |
| 7,244,934 B2 | 7/2007 | Arnone et al. | |
| 7,291,835 B2 | 11/2007 | Overney | |
| 7,291,839 B1 | 11/2007 | Demers et al. | |
| 7,335,883 B2 | 2/2008 | Wallace et al. | |
| 7,439,511 B2 | 10/2008 | Demers | |
| 7,485,863 B2 | 2/2009 | Cole | |
| 7,535,005 B2 | 5/2009 | Demers | |
| 7,781,736 B2 * | 8/2010 | Logan et al. | 250/339.07 |
| 7,804,069 B2 | 9/2010 | Tribe | |
| 7,936,453 B2 | 5/2011 | Logan, Jr. et al. | |
| 7,963,571 B2 | 6/2011 | Martin | |
| 8,138,477 B2 | 3/2012 | Gregory | |
| 8,604,433 B2 | 12/2013 | Logan, Jr. et al. | |
| 2003/0155512 A1 | 8/2003 | Arnone et al. | |
| 2004/0065831 A1 | 4/2004 | Federici et al. | |
| 2005/0162658 A1 | 7/2005 | Pepper | |
| 2006/0084180 A1 | 4/2006 | Paldus et al. | |
| 2006/0214107 A1 | 9/2006 | Mueller | |
| 2006/0255277 A1* | 11/2006 | Cole et al. | 250/341.1 |
| 2008/0179519 A1 | 7/2008 | Andonian et al. | |
| 2008/0179528 A1 | 7/2008 | Demers | |
| 2008/0212974 A1 | 9/2008 | Davies et al. | |
| 2008/0251720 A1 | 10/2008 | Xu et al. | |
| 2009/0015843 A1 | 1/2009 | Demers et al. | |
| 2009/0066948 A1 | 3/2009 | Karpowicz et al. | |
| 2009/0091820 A1 | 4/2009 | McCarthy et al. | |
| 2009/0180122 A1 | 7/2009 | Federici | |
| 2009/0200472 A1 | 8/2009 | Gregory | |
| 2009/0283680 A1 | 11/2009 | Logan, Jr. et al. | |
| 2010/0080505 A1 | 4/2010 | Sartorius et al. | |
| 2010/0092183 A1 | 4/2010 | Kim et al. | |
| 2010/0171835 A1 | 7/2010 | Kasai et al. | |
| 2011/0032955 A1 | 2/2011 | Daiber | |
| 2011/0068268 A1 | 3/2011 | Heidari | |
| 2012/0075477 A1 | 3/2012 | Daly et al. | |
| 2012/0326039 A1 | 12/2012 | Demers et al. | |
| 2013/0200263 A1 | 8/2013 | Logan et al. | |
| 2014/0021351 A1 | 1/2014 | Logan et al. | |
| 2014/0043612 A1 | 2/2014 | Logan, Jr. et al. | |

FOREIGN PATENT DOCUMENTS

| | | |
|---|---|---|
| GB | 2483118 | 2/2012 |
| WO | WO 2007/135382 A2 | 11/2007 |
| WO | WO 2009/082820 A1 | 7/2009 |
| WO | WO 2009/137263 A2 | 11/2009 |
| WO | WO 2009/137263 A3 | 1/2010 |

OTHER PUBLICATIONS

Intellectual Property Office Search Report for Application No. GB10170462 dated Nov. 16, 2010; 1 page.

Izutsu et al., "Integrated Optical SSB Modulator/Frequency Shifter," *IEEE Journal of Quantum Electronics*, Nov. 1981, QE-17:2225-2227.

U.S. Appl. No. 14/054,599, filed Oct. 15, 2013, Logan et al.

Arnone et al., "Applications of Terahertz (THz) Technology to Medical Imaging," *Proc. SPIE Terahertz Spectroscopy Applicat. II*, 1999; 3823:209-219.

Arnone et al., "Terahertz Imaging Comes Into View," *Phys. World*, 2000; pp. 35-40.

Bartels et al., "Femtosecond Time-Resolved Optical Pump-Probe Spectroscopy at Kilo Rates Over Nanosecond-Time-Delays Without Mechanical Delay Line," *Appl. Phys. Lett.*, 2006; 88:04117.

Bartels et al., "High-Resolution THz Spectrometer with kHz Scan Rates," *Optics Express*, 2006; 14(1):430-437.

Bjanason et al., "ErAs:GaAs Photomixer with two decades tenability and 12 μW Peak Output," *Applied Physics Letters*, 2004; 85(18):3983-3985.

Chang et al., "Power Scalable Compact THz System Based on an Ultrafast Yb-doped Fiber Amplifier," *Optics Express*, 2006; 14(17):7909-7913.

Chen et al., "Spectroscopic Applications and Frequency Locking of THz Photomixing with Distributed-Bragg-Reflector Diode Lasers in LowTemperature-Grown GaAs," *Appl. Phys. Lett.*, 1997; 71(12):1601-1603.

Combined Search and Examination Report for Application No. GB1309663.1 dated Nov. 13, 2013; 8 pgs.

Demers et al., "An Optically Integrated Coherent Frequency-Domain THz Spectrometer with Signal-to-Noise Ratio up to 80 dB," 2007 IEEE Conference; pp. 92-95.

Gutierrez, "An Electro-Optical Frequency Shifter," NASA's Jet Propulsion Laboratory, 2000; Available at <URL:http://www.nasatech.com/Briefs/Sept00/NPO20531.html>.

Hu et al., "Imaging with Terahertz Waves," *Optics Letters*, 1995; 20(16):1716-1718.

Hunsche et al., "Terahertz 'T-Ray' Tomography," *Proc. SPIE Int. Millimeter Submillimeter Waves Applicat. IV.*, 1998; 50(3):426-433.

Janke et al., "Asynchronous Optical Sampling for High-Speed Characterization of Integrated Resonant Terahertz Sensors," *Optics Letters*, 2005; 3 0(11):1405-1407.

Jiang et al., "Terahertz Imaging via Eletrooptic Effect," *IEEE Trans. Microwave Theory Tech.*, 1999; 47:2644-2650.

McGrath et al., "Superconducting Hot Electron Mixers with Ultra Wide RF Bandwidth for Heterodyne Receiver Applications Up to 3 THz," *Proceedings of the ESA Symposium*, 1997; pp. 401-404.

McIntosh et al., "Terahertz Measurements of Resonant Planar Antennas Coupled to Low-Temperature-Grown GaAs Photomixers," *Appl. Phys. Lett.*, 1996; 69(24):3632-3634.

Mittleman et al., "T-Ray Imaging," *IEEE J. Select. Topics Quantum Electron*, 1996; 2:679-692.

Saleh et al., "Fundamentals of Photonics," Wiley-Interscience, 1991; pp. 719-720, 823-825.

Search Report, app. No. GB10170462. Intellectual Property Office, UK.

Siegel, "Terahertz Technology," *IEEE Transactions on Microwave Theory and Techniques*, 2002; 50(3):915-917.

Verghese et al., "Generation and Detection of Coherent Terahertz Waves Using Two Photomixers," *Applied Physics Letters*, 1998; 73(26):3824-3826.

Wu et al., "Two-Dimensional Electro-Optic Imaging of THz Beams," *Appl. Phys. Lett.*, 1996; 69(8):1026-1028.

Yasui et al., "Terahertz Frequency Comb by Multifrequency-Heterodyning Photoconductive Detection for Hig-Accuracy, High Resolution Terahertz Spectroscopy," *Applied Physics Letters*, 2006; 88(241104):1-3.

Demers et al., "Field-portable THz Spectrometer for Characterization of Explosives and Chemicals," IEEE IRMMW Conference, Houston, TX, Oct. 6, 2011; 26 pgs.

Logan, Jr. et al., "Field-portable THz Spectrometer for Characterization of Explosives and Chemicals," Emcore Corporation Conference Publication, Oct. 2011; 3 pgs.

* cited by examiner

9,029,775 B2

TERAHERTZ FREQUENCY DOMAIN SPECTROMETER WITH PHASE MODULATION OF SOURCE LASER BEAM

REFERENCE TO RELATED APPLICATIONS

This application is a continuation-in-part of U.S. patent application Ser. No. 12/861,651, filed Aug. 23, 2010, which in turn is a continuation-in-part of U.S. patent application Ser. No. 12/465,219, filed May 13, 2009, now U.S. Pat. No. 7,781,736, which application claims priority of U.S. Provisional Application Ser. No. 61/054,344 filed May 19, 2008. Each of these applications is herein incorporated by reference in its entirety.

BACKGROUND OF THE INVENTION

1. Field of the Invention

The invention relates to microwave, millimeter wave and submillimeter wave spectroscopy systems and components and in particular to an apparatus and method for modulating or adjusting the phase of the optical beam directed to the source photomixer used in a transceiver for terahertz spectroscopy.

2. Description of the Related Art

Terahertz devices and systems generally employ electromagnetic energy between 300 GHz and 3 terahertz (3 THz), or wavelengths from 100 to 1000 microns (0.1 to 1.0 millimeters), which is also referred to as the submillimeter or far-infrared region of the electromagnetic spectrum.

One important application of terahertz systems is THz spectroscopy. Terahertz spectroscopy presents many new instrumentation and measurement applications since certain compounds and objects can be identified and characterized by a frequency-dependent absorption, dispersion, and/or reflection of terahertz signals which pass through or are reflected from the compound or object.

The generation of terahertz radiation by photomixing is a method of generating quasi-optical signals using an optical-heterodyne converter or photomixer. Typical photomixer devices include low-temperature-grown (LTG) GaAs semiconductor devices, which have been used to generate coherent radiation at frequencies tip to 5 THz. The spectroscopy system typically uses two single frequency tunable lasers, such as diode lasers, to generate two optical laser beams which are directed at the surface of the photomixer. By photoconductive mixing of the two beams in the semiconductor material, a terahertz difference frequency between the two optical laser frequencies is generated. In particular, a first laser generates radiation at a first frequency and a second laser generates radiation at a second frequency. The difference frequency, equal to the difference between the first and the second laser frequencies, is swept by the user from microwave through terahertz frequencies by changing the temperature of the lasers, which coarsely changes the frequency of one or both lasers. Other types of tuning mechanisms exist, such as distributed-Bragg-reflector diode lasers with multiple electrodes, grating-loaded external cavities, etc. A terahertz transmitter includes a first photomixer that is optically coupled to the first and the second light source. A first radiative element or antenna is electrically coupled to the first photomixer. In operation, the first antenna radiates a terahertz signal generated by the first photomixer at the difference frequency. A receiver includes a second antenna positioned to receive the signal from the target radiated by the first antenna. The second antenna generates a time varying voltage proportional to the terahertz return signal. A second photomixer is electrically coupled to the second antenna and is optically coupled to the first and the second light source. The second photomixer generates a homodyne downconverted current signal in response to the time varying voltage generated by the second antenna. The downconverted signal is a measurement of the absorption or reflection of the sample material at each terahertz frequency. This is useful, for example, when used in conjunction with computer processing to identify unknown samples by comparing measured results to a library of reference spectra. This apparatus may also be used to characterize the frequency response characteristics of passive or active components and devices such as waveguides, filters, amplifiers, mixers, diodes, and the like designed to work at terahertz frequencies.

SUMMARY OF THE INVENTION

1. Objects of the Invention

It is an object of the present invention to provide an improved frequency domain terahertz spectrometer using two continuously tunable semiconductor lasers with the phase of the optical beam applied to the source or detection photoconductive switch being electronically modulated or adjustable.

It is another object of the present invention to provide a terahertz spectrometer for the identification of a target spectrum with high resolution and detection sensitivity of absorption bands of interest by producing CW radiation in one or more frequency bands, and "fine tuning" the terahertz radiation in at least some of those bands to identify a spectral signature by phase modulation.

It is also another object of the present invention to mitigate the interference effect in a frequency domain terahertz spectrometer with finely controllable phase difference between the mixing laser beams by periodically modulating the phase.

It is also another object of the present invention to eliminate the shift in interference patterns as a result of movement of the source or detector relative to the target.

It is an object of the present invention to provide a method for independently adjusting the phase difference between two source lasers forming a composite optical beam used in a frequency domain terahertz spectrometer.

It is another object of the present invention to provide a method for adjusting the phase of a laser in a terahertz spectrometer using photoconductive switches to provide more accurate frequency specificity and resolution by "fine tuning" the terahertz radiation in a frequency band of interest using a phase modulator and a reference oscillator.

It is also another object of the present invention to provide a terahertz spectrometer with adjustable resolution of the order of a MHz or 10's of MHz at specific frequency bands or absorption regions of interest by phase modulation.

It is another object of the present invention to provide a method for adjusting the phase of a laser in a terahertz spectrometer using photoconductive switches to provide more accurate frequency specificity and resolution by "fine tuning" the terahertz radiation in a frequency band of interest.

It is still another object of the present invention to provide a self-contained, field portable terahertz spectrometer system in a highly compact configuration capable of identifying or imaging an object utilizing a laser with an electronically adjustable or controllable phase.

It is also another object of the present invention to provide a terahertz spectrometer with adjustable resolution of the order of MHz or 10's of MHz at specific frequency bands or absorption regions of interest by adjusting the step or increment size of the frequency sweep.

It is also another object of the present invention to provide a terahertz spectrometer with adjustable signal to noise ratio of the order of 10 dB-Hz to 100 dB-Hz at specific frequency bands or absorption regions of interest by adjusting the time constant of the lock-in amplifier.

It is also another object of the present invention to provide a terahertz spectrometer with adjustable resolution of the order of MHz or 10's of MHz at specific frequency bands or absorption regions of interest by adjusting the interference pattern.

It is also another object of the present invention to provide a terahertz spectrometer with adjustable resolution of the order of MHz or 10's of MHz at specific frequency bands or absorption regions of interest by adjusting the time period over which the sweep takes place.

It is also another object of the present invention to provide a terahertz spectrometer with adjustable resolution of the order of MHz or 10's of MHz at specific frequency bands or absorption regions of interest by performing a phase sweep at a constant frequency.

It is also another object of the present invention to provide a terahertz spectrometer with adjustable resolution of the order of MHz or 10's of MHz at specific frequency bands or absorption regions of interest by adjusting the resolution in the frequency sweep.

Some implementations may achieve fewer than all of the foregoing objects.

2. Features of the Invention

Briefly, and in general terms, the present disclosure provides an apparatus for analyzing, identifying or imaging a target, including first and second lasers having tunable frequencies, the first laser to produce a first output beam and the second laser to produce a second output beam, the first output beam and the second output beam having different optical frequencies; a phase modulator positioned to receive a first portion of the first output beam to controllably modulate the phase of the first output beam and producing an modulated output third beam; a first optical element coupled to the modulated output third beam and to a portion of the second beam to produce a composite output fourth beam; a source of CW signals in a range of frequencies from 100 MHz to over 2 THz including a first photoconductive switch activated by the composite output fourth beam; a radiative element coupled to the source of CW signals for causing the CW signals to be substantially simultaneously focused on or through the target; a second optical element coupled to a portion of the first beam and to a portion of the second beam to produce a composite output fifth beam; and a detector for acquiring spectral information from said target and coupled to the composite output fifth beam, and generating, based on said spectral information and the composite output fifth beam, an electrical signal representative of a characteristic of the target.

In another aspect, the disclosure provides an apparatus for analyzing, identifying or imaging an object, including a source of CW signals with an adjustable phase in a range of frequencies greater than 100 MHz directed to said object; and a detector for acquiring spectral information reflected from or transmitted through said object and performing a heterodyne down conversion for generating an electrical signal representative of some characteristics of the object.

In another aspect, the disclosure provides a method for analyzing, identifying or imaging an object, including generating CW signals in a range of frequencies lying above 100 MHz utilizing a phase modulator with a reference oscillator and directing the CW signals to said object; and acquiring spectral information reflected from or transmitted through said object and performing a heterodyne down conversion using a lock-in signal from the reference oscillator for generating an electrical signal representative of some characteristics of the object.

In another aspect, the disclosure provides a method for analyzing, identifying or imaging a target by providing first and second lasers having first and second output beams respectively having different frequencies; periodically phase modulating the first output beam to produce a third beam; generating a CW radiative beam using a first photoconductive switch in the range of frequencies greater than 100 MHz from the first and third beams; causing the CW radiative beam to be substantially simultaneously focused on or through the target; combining the first beam and the second beam into a composite fourth beam; acquiring a spectral information signal from said target using a second photoconductive switch activated by said composite fourth beam; and generating an electrical signal representative of a characteristic of said target using said spectral information signal and said composite fourth beam.

In another aspect, the disclosure provides a method comprising providing first and second lasers having tunable frequencies for producing a first optical beam and a second optical beam respectively with different frequencies; phase shifting or modulating the first optical beam to produce a finely adjustable phase shifted third optical beam; producing a composite fourth beam from the second and the third optical beams; producing a composite fifth beam from the first and the second optical beams; coupling the fourth optical beam to a first photoconductive switch for producing a CW radiative beam in a range of frequencies greater than 100 MHz; directing the CW radiative beam to be focused on or through a target; and detecting the radiative beam reflected from or transmitted through the target by a second photoconductive switch coupled to the composite fifth optical beam; and generating an electrical signal representative of some characteristic of the target.

In another aspect, the disclosure provides a method for terahertz spectroscopy including sweeping a source of CW radiative beams over a range of frequencies greater than 100 MHz, including a first photoconductive switch activated by a first composite optical laser beam; directing the radiative beam to be focused on a target; and acquiring spectral information from the target by a second photoconductive switch coupled to a second composite optical beam; and adjusting the phase difference between the first composite beam and the second composite optical beam by a phase modulator in the path of the first optical beams used to generate the first composite optical beam, for generating additional electrical signals representative of some characteristic of the target in a selected frequency band.

In another aspect, the disclosure provides a method for terahertz spectroscopy including sweeping, both in frequency and in phase, a source of CW radiative beams in one or more predetermined frequency bands lying in a range of frequencies greater than 100 MHz; acquiring spectral information from the target; and processing the spectral information to determine the presence of a specific spectral signature to identify a compound of interest.

The phase modulator may be a lithium niobate modulator.

The phase modulation of the CW signals by the phase modulator may result in a constructive or destructive interference of the THz beam and the composite output fifth beam on the detector.

A signal source may be coupled to the phase modulator to allow the first output beam to be swept in phase over 360 degrees.

The frequency of the signal source may be selectable to allow the operator to analyze a specified frequency band of interest.

The signal source coupled to the phase modulator may be swept in phase as the first output beam is swept in frequency.

A heterodyne detection system may be provided that includes a lock-in amplifier coupled to the detector, wherein the signal source coupled to the phase modulator is also coupled to the lock-in amplifier.

The source of CW signals may include a first photoconductive switch activated by the composite output fourth beam.

The first and second lasers may be disposed in a first housing, and the first photoconductive switch may be disposed in a second housing separate from and spaced apart from the first housing, wherein the first housing and the second housing are coupled by an optical fiber.

The first and second lasers may be disposed in a first housing, and the detector may be disposed in a third housing separate from and spaced apart from the first housing, wherein the first housing and the third housing are coupled by an optical fiber.

A power source, keypad, and display may be disposed in the first housing.

A processor may be disposed in the first housing for determining a characteristic of the target based upon the absorption characteristics of the target in a frequency range in the 100 MHz to over 2 THz frequency band.

The detector may include a second photoconductive switch activated by a second composite optical beam from the first and second lasers that is offset in frequency from the first composite optical beam.

The first and second photoconductive switches may be low temperature grown GaAs photoconductive switches.

The first and second thermoelectric coolers may be coupled to the first and second lasers, respectively, for independently coarsely tuning each of the lasers over a wavelength range of about 5 nm in intervals or step sizes of about 0.0001 nm.

The first and second lasers may be DFB or DBR lasers tuned to different frequencies.

The first and second lasers may be external cavity lasers.

The first optical element may be a waveguide coupler.

The first photoconductive switch may be biased with a constant electrical potential.

The phase modulator may be a lithium niobate device.

The signal applied to the phase modulator may be a periodic 6 kHz signal.

The lock-in amplifier may be locked to the signal applied to the phase modulator.

In another aspect, the disclosure provides a method for analyzing, identifying or imaging a target, comprising generating CW beams in a range of frequencies lying between 100 MHz to over 2 THz; sweeping, both in frequency and in phase, the CW radiative beams in one or more predetermined frequency bands; directing the radiative beams to the target; and acquiring spectral information reflected from or transmitted through the target.

The CW radiative beams may be periodically swept in phase over 360 degrees.

The acquisition of spectral information may include use of a heterodyne detection system including a lock-in amplifier that is coupled to the detector and performing a lock-in of the detected signal to a signal applied to the phase modulator.

A signal source periodically swept in phase over 360 degrees may be coupled to the lock-in amplifier.

The signal source periodically swept in phase over 360 degrees is swept at a rate at least twice as fast as the frequency sweeping rate of the laser.

The phase modulation of the CW radiative beam by a phase modulator results in an interference insensitivity, i.e. the detected signal is independent of the distance between the source and the target.

The phase modulation of the CW radiative beam by a phase modulator results in the removal of the interference pattern.

In another aspect, the disclosure provides a method for analyzing, identifying or imaging a target, comprising generating CW signals in a range of frequencies lying between 100 MHz to over 2 THz and directing them to the target; and acquiring spectral information reflected from or transmitted through said object and performing a heterodyne down conversion for generating an electrical signal representative of some characteristics of the target.

The first and second lasers may have different tunable frequencies, and wherein the frequency of at least one of the lasers is swept or tuned over a frequency range of at least 800 GHz with a step size of at least 2 GHz so as to produce a swept CW radiative beam in a range of frequencies lying between 100 MHz to over 2 THz directed to the target, and the phase of the laser is swept at a rate at least twice as fast as the frequency sweeping rate.

In another aspect, the disclosure provides a method for terahertz spectroscopy including sweeping, in frequency over a selectable frequency range, a source of CW radiative beams in one or more predetermined frequency bands lying in a range of frequencies greater than 100 MHz; acquiring spectral information from the target; and processing the spectral information to determine the presence of a specific spectral signature to identify a compound of interest.

In another aspect, the disclosure provides a method for terahertz spectroscopy including sweeping, in a selectable set of frequencies, a source of CW radiative beams in one or more predetermined frequency bands lying in a range of frequencies greater than 100 MHz; acquiring spectral information from the target; and processing the spectral information to determine the presence of a specific spectral signature to identify a compound of interest.

In another aspect, the disclosure provides a method for terahertz spectroscopy including sweeping, in a frequency band with a selectable step or increment size, a source of CW radiative beams in one or more predetermined frequency bands lying in a range of frequencies greater than 100 MHz; acquiring spectral information from the target; and processing the spectral information to determine the presence of a specific spectral signature to identify a compound of interest.

In another aspect, the disclosure provides a method for terahertz spectroscopy including sweeping, in frequency over a selectable time period, a source of CW radiative beams in one or more predetermined frequency bands lying in a range of frequencies greater than 100 MHz; acquiring spectral information from the target; and processing the spectral information to determine the presence of a specific spectral signature to identify a compound of interest.

In another aspect, the disclosure provides a method for terahertz spectroscopy including sweeping, in a frequency band with a selectable resolution, a source of CW radiative beams in one or more predetermined frequency bands lying in a range of frequencies greater than 100 MHz; acquiring spectral information from the target; and processing the spectral information to determine the presence of a specific spectral signature to identify a compound of interest.

In another aspect, the disclosure provides a method for terahertz spectroscopy including sweeping a source of CW radiative beams in one or more predetermined frequency bands lying in a range of frequencies greater than 100 MHz; acquiring spectral information from the target; and processing the spectral information with a lock-in amplifier with an adjustable time constant to determine the presence of a specific spectral signature to identify a compound of interest.

In another aspect, the disclosure provides a method for terahertz spectroscopy including sweeping a source of CW radiative beams in one or more predetermined frequency bands lying in a range of frequencies greater than 100 MHz; acquiring spectral wherein information from the target; and processing the spectral information with means for adjusting the interference pattern to determine the presence of a specific spectral signature to identify a compound of interest.

In the sweeping process, the step size may be selected by the user to a selected value, as an example, in some embodiments, to a value between 100 MHz to 5 GHz.

In the sweeping process, the number of frequencies may be selected by the user to a selected value, as an example, in some embodiments, to a value between 100 and 2000.

In the sweeping process, the time period of the sweep may be selected by the user to a selected value, as an example, in some embodiments, to a value between 10 seconds and 1000 seconds.

In the sweeping process, the step size, the number of frequencies, and the time period of the sweep, may be adjusted to achieve a given resolution and signal to noise ratio.

Some implementations or embodiments may incorporate or implement fewer of the aspects or features noted in the foregoing summaries.

Additional objects, advantages, and novel features of the present invention will become apparent to those skilled in the art from this disclosure, including the following detailed description as well as by practice of the invention. While the invention is described below with reference to preferred embodiments, it should be understood that the invention is not limited thereto. Those of ordinary skill in the art having access to the teachings herein will recognize additional applications modifications and embodiments in other fields, which are within the scope of the invention as disclosed and claimed herein and with respect to which the invention could be of utility.

BRIEF DESCRIPTION OF THE DRAWINGS

These and other features and advantages of this invention will be better understood and more fully appreciated by reference to the following detailed description when considered in conjunction with the accompanying drawings wherein.

Figure 1A:
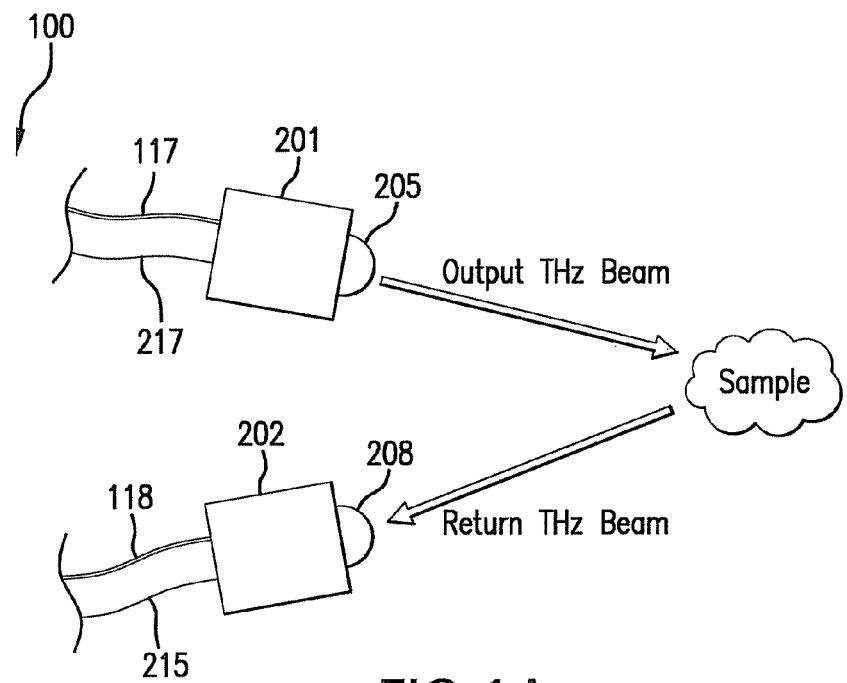
FIG. 1A is a block diagram of a frequency domain terahertz spectrometer according to the present disclosure which employs reflection from the sample.

The novel features and characteristics of the disclosure are set forth in the appended claims.

DETAILED DESCRIPTION OF THE PREFERRED EMBODIMENT

Details of the present disclosure will now be described, including exemplary aspects and embodiments thereof.

Referring to the drawings and the following description, like reference numbers are used to identify like or functionally similar elements, and are intended to illustrate major features of exemplary embodiments in a highly simplified diagrammatic manner. Moreover, the drawings are not intended to depict every feature of actual embodiments or the relative dimensions of the depicted elements, and are not drawn to scale.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As noted above, in the frequency domain technique for terahertz spectroscopy, CW THz radiation is produced through photomixing of the combined output of two single-frequency diode lasers in a low temperature grown GaAs photomixer or PCS. The wavelength of one (or both) of the lasers is tuned by temperature adjustment of the laser to coarsely vary the THz output frequency, which may therefore be swept over one or more frequency bands of interest for characterizing the target or sample material.

In most frequency domain spectrometers, coherent (homodyne) detection can be achieved at room temperature by mixing the same optical radiation from the diode lasers in a detector PCS onto which the return THz signal is also incident. This provides similar or greater sensitivity and faster data acquisition than the incoherent technique.

Figure 1B:
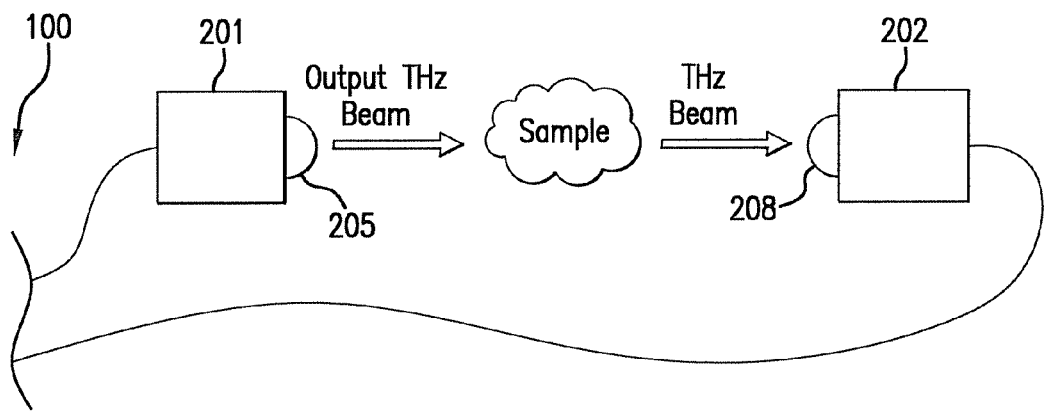
FIG. 1B is a block diagram of a frequency domain terahertz spectrometer according to the present disclosure which employs transmission from the sample.

In a terahertz spectrometer, the terahertz radiation is focused or directed to the target sample to be analyzed, and a detector or detector array is arranged to collect the signal propagated through or reflected from that target. The two modes of transmission or reflection from the target are illustrated in FIG. 1A and 1B. The configuration or arrangement of FIG. 1A depicts reflection, and FIG. 1B depicts transmission through the target or sample by appropriate placement of the source head or module 201 and the detector head or module 202. A housing 100 (shown in FIG. 2) incorporates the user interface and the optical and electro-optical components associated with the coupled spectrometer heads of FIG. 1A and 1B. In one embodiment of the present disclosure, the modules 201 and 202 are enclosed in different housings, each of which may be manually moved or positioned by the operator with respect to the sample under test. A fiber optic cable 117 and an electrical cable 217 couple the housing 100 to the module 201, and fiber optic cable 118 and an electrical cable 215 couple the housing 100 to the module 202. The silicon lens 205 on the exterior of the housing 201 enables the terahertz radiation to be focused or directed to the target by the user, and the silicon lens 208 on the exterior of the housing 202 is positioned by the user so that it collects the radiation transmitted or reflected from the target. It is noted that additional optical elements including but not limited to lenses, focusing mirrors, parabolic reflectors, sub-reflectors, beam-splitters/combiners, and beam-shaping optics (not shown for clarity) may also be employed to provide focusing or manipulation of the radiated terahertz beams, as the particular measurement situation requires.

FIG. 1B is a block diagram of a representative spectrometer arranged to employ transmission through the sample. The operation of the various components are substantially identical to the operation in FIG. 1A, and need not be repeated here.

The figure illustrates how the source and detector housings 201 and 202 may be manually moved and positioned by the operator with respect to the target. Alternatively, the source and detector housings 201 and 202 may be combined into one common housing.

Figure 2:
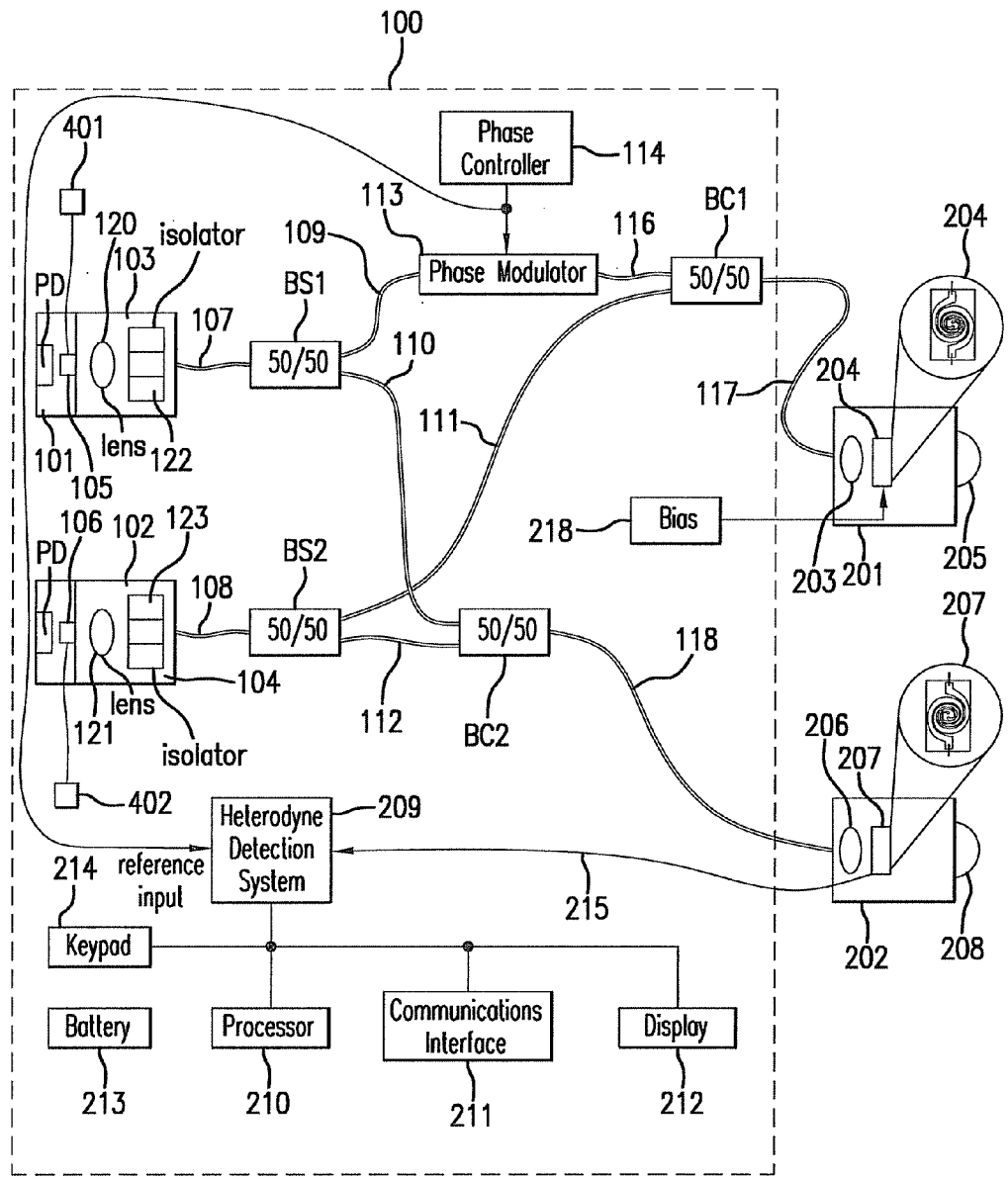
FIG. 2 is a block diagram of a frequency domain terahertz spectrometer of the present disclosure.

Turning to FIG. 2, there is depicted a housing 100 incorporating the optical and electro-optical components suited for use as a subassembly in conjunction with the coupled spectrometer heads of FIG. 1A and 1B. In some embodiments, the housing is sized and designed to be lightweight and portable, and worn or supported by the user during operation. Laser subassemblies 101 and 102 include lasers 105 and 106, respectively, which are preferably two 783 nm distributed feedback (DFB) or distributed Bragg reflector (DBR) semiconductor laser diodes with single-longitudinal-mode and single spatial-mode operation over the desired range of wavelengths, available from various vendors (for example, Eagleyard Photonics GmbH of Berlin, Germany, or Photodigm, Inc. of Richardson, Tex.). In some embodiments it would also be possible to utilize one or more packaged external-cavity tunable semiconductor lasers such as are available from Emcore Corporation, of Newark, Calif., such as disclosed in U.S. patent application Ser. No. 12/722,825, filed Mar. 12, 2010. In one embodiment, the output of one laser is adjusted to 783 nm, and the output of the other laser is adjusted to 784 nm. The diode laser packaging permits co-collimation of the laser beams to a very high degree of precision, and the design allows very precise frequency control of the lasers by temperature and/or electronic tuning, and monitoring the laser output through digital signal processing, to achieve more accurate control over the laser output beam frequencies.

In one embodiment, the laser diode chips 105 and 106 are mounted on independent Peltier thermoelectric coolers (TECs) 103 and 104. The center wavelengths of the lasers are nominally 783 nm at 25° C., but the wavelengths may be coarsely temperature-tuned with a tuning coefficient of approximately 0.1 nm per ° C. Therefore, a 50 degree C. temperature range of operation from −10 degrees C. to +40 degrees C. will yield a frequency range of approximately 5 nm. For the purposes of illustration only, if the DFB lasers are selected such that their center wavelengths at 25 degrees C. are at 782 nm and 784 nm, respectively, then a thermal tuning range of −10 degrees C. to +40 degrees C. on each laser chip will permit generation of offset wavelengths 0 nm to approximately 7 nm, corresponding to a range of offset frequencies from 0 Hz to 3.4 THz. The thermal mass on the controlled surface of the TECs is such that it allows rapid frequency tuning. In the case of DBR laser diode chips, the Bragg-reflection section of each laser may be adjusted electronically to vary the laser frequency. Wider offset frequency ranges may also be possible by employing wider temperature excursion, or by using DBR or external cavity lasers.

The output beam from each laser 105, 106 is collimated with an aspheric lens 120, 121 respectively, mounted on a precision lens-mount with sub-micron adjustment capability (see, e.g. U.S. Pat. No. 7,126,078). After passing through the lens, the laser output beams are directed through a respective optical isolator 122 and 123, to prevent feedback into the laser, and to couple the output beam to pigtail optical fibers 107 and 108, respectively.

A 50/50 waveguide coupler or beamsplitter BS1 and BS2 are coupled to the pigtail optical fibers 107 and 108, respectively, and the output beams on fibers 107 and 108 are each split into composite primary and secondary beams 109 and 110, and 111 and 112 respectively.

In the embodiment depicted in the present disclosure, the primary output beam 109 is directed along a fiber or first path to a phase control element such as a phase modulator 113. The phase modulator 113 may be an lithium niobate device, such as those manufactured by Photline Technologies of Besancon, France. The phase modulator 113 allows the user to sweep the phase automatically (by pre-programmed software) or manually adjust the phase of the laser output beam 109 in a highly precise manner, thereby also adjusting the phase of the emitted CW terahertz beam. The output of the phase modulator 113 is then coupled to a waveguide coupler or beamcombiner BC1. In some embodiments, the signal applied to the phase modulator is a periodic 6 kHz signal, or more generally, a periodic signal that is swept at a rate at least twice as fast as the rate at which the laser frequency is swept.

A tunable reference oscillator 114 is connected to the phase modulator 113 for sweeping or precisely incrementing or decrementing the phase by a periodic or other type of signal.

The beam 110 is directed along a fiber or first path to a waveguide coupler or beamcombiner BC2, and similarly the beam 112 is directed along a fiber or first path to the waveguide coupler or beamcombiner BC2. The output beam from beamsplitter BS2 is directed along a fiber 118 or first path so as to exit the module 100 and is subsequently directed by fiber 118 to the detector head 202.

The output beam 111 from beamsplitter BS2 is directed along a fiber or first path to the beamcombiner BC1. The output of the phase modulator 113 is directed along fiber 116 to the beamcombiner BC1. The output of beamcombiner BC1 is then applied to fiber 117 which exits the module 100 and is subsequently directed to the source head 201.

The optical propagation path downstream of the lasers and throughout the unit 100 may be an appropriate single-mode polarization-maintaining optical fiber (PMF) or free space. In the case of optical fiber construction, the beamsplitters may be replaced with suitable optical waveguide couplers. As can be appreciated, the basic topology depicted in FIG. 2 uses fiber optical implementation which readily illustrates the various optical paths, while FIG. 4 will illustrate a free space implementation.

The beam from beamcombiner BC1 is coupled to a fiber 117 which is then coupled to the external source head 201, as described above. In source head 201, the composite output beam of the two distinct laser sources is then applied to a lens 203 which focuses the beam to a spot of approximately ten microns in diameter on the surface of a low temperature grown (LTG) gallium arsenide (GaAs) photoconductive switch (PCS) 204. The two optical beams are combined or photomixed in the PCS 204. Other types of photoconductive switches may be used as well. The laser beam may be focused at a gap in an antenna circuit patterned on the surface of the PCS, which in some embodiments is implemented as the spiral as shown in FIG. 2, with the gap located at the center of the spiral. A constant DC electrical bias coupled to the source head by cable 217 may also be applied across the terminals of the antenna on the PCS. In some embodiments, as known in the prior art, a slowly time-varying (i.e., "chopped") electrical bias signal may be applied across the terminals of the antenna on the PCS.

The terahertz variation in the intensity of the mixing or difference signal between the two laser frequencies, often referred to as the "heterodyne laser signal", produces a terahertz modulation of the conductance in the PCS material, which in turn produces a terahertz current flow in the antenna patterned on the surface of the PCS. This current in the antenna produces an electromagnetic field, i.e. terahertz radiation, propagating into the surrounding space and having a frequency range from typically 100 MHz to over 2 THz, depending on the difference frequency of the two laser sources. The terahertz radiation so produced is emitted from PCS device 204 and then collimated and collected by a silicon lens 205, preferably a hemispherically shaped structure approximately two to three centimeters in diameter. Additional lenses (not shown), composed of TEFLON™ or other suitable materials may be placed downstream of the lens 205 to collimate the RF beams into an output terahertz beam. Beam-shaping mirrors may also be used in lieu of or in addition to the silicon lens 205 in the source head 201.

The outgoing terahertz radiation beam from currently available PCS devices is relatively low power, about 1 to 10 microwatts. The target sample (not shown) is typically positioned relatively close to the source and detector heads, and will absorb and transmit some terahertz radiation, and also reflect a portion of the terahertz radiation back in the direction of the source or user, as shown by the return THz beam in FIG. 1A.

On the receiver side of the spectrometer, the beam from beamcombiner BC2 is coupled to a fiber 118 which is then coupled to the external detector head 202, as described above. In detector head 202, the composite output beam of the two distinct laser sources is then applied to a lens 206 which focuses the beam to a spot of approximately ten microns in diameter on the surface of a low temperature grown (LTG) gallium arsenide (GaAs) photoconductive switch (PCS) 207. The two optical beams are combined or photomixed in the PCS 207. Other types of photoconductive switches may be used as well. The laser beam may be focused at a gap in an antenna circuit patterned on the surface of the PCS 207, which in some embodiments is implemented as the spiral as shown in FIG. 2, with the gap located at the center of the spiral. In some embodiments the spiral antenna on the detector PCS 207 is implemented in a clockwise direction, in contrast to the counter-clockwise direction of the spiral antenna on the source PCS 204.

The terahertz return signal from the sample or target is captured by a suitably positioned second silicon lens 208 in the detector head 202, which focuses the return terahertz beam to the antenna on the surface of PCS 207 which acts as a terahertz radiation detector.

In the prior art embodiments, the terahertz variation in the intensity of the mixing or difference signal between the two laser frequencies, in combination with the terahertz modulation of the conductance in the PCS material, as a result of the terahertz current flow in the antenna from the received terahertz signal from the sample, results in a homodyne down conversion of the received terahertz signal to a baseband frequency equal to the "chopping" frequency, that may then be detected by a synchronous circuit such as a "lock-in" amplifier, or similar arrangement.

In embodiments contemplated by the present disclosure, the terahertz variation in the intensity of the mixing or difference signal between the two laser frequencies, in combination with the terahertz modulation of the conductance in the PCS material as a result of the terahertz current flow in the antenna from the received terahertz signal from the sample, results in a heterodyning and down conversion of the received terahertz signal to a baseband frequency equal to the frequency of the reference oscillator 114. The synchronous detection circuit makes use of the reference oscillator 114 signal applied to the phase modulator 113, and thereby to the signal applied to source PCS 204, as a reference for the synchronous detection process.

A signal resulting from this heterodyne detection system 209 may be coupled to and processed by processor 210. The spectrometer may further incorporate software for automatically determining the identity or composition of the target, and other electronic elements for printing or displaying the results so that the analysis, identification, or image information is readily available to the user. FIG. 2 illustrates a communications interface (which may be a wireless RF transceiver for communicating the results to an external user or network element) 211, a display 212, and a keypad 214 as examples of elements providing user or operator interface. A battery 213, or other self-contained power source, may be provided to make the unit field portable.

In one embodiment, the frequency of one of the lasers, and consequentially the radiative terahertz frequency, is swept or tuned through a series of frequencies, or through a sequence of distinct specific frequency bands. The return terahertz signal $S_{out}$ is collected by the detector and transferred to processor 210 for data collection and analysis at each specific frequency of interest. In this way, the absorption or reflection spectrum of the sample under test can be collected with high resolution and high signal-to-noise ratio since all of the terahertz energy is centered in a single tone and the lock-in amplifier limits the noise bandwidth. This, incidentally, is a major advantage of the frequency domain technique compared to time-domain techniques in which the terahertz energy is spread over many frequencies. In some embodiments, the tuning and terahertz emission may be adapted to a specific sequence or set of frequency bands having spectral absorption peaks corresponding to the unique spectral signature of a particular material of concern. Thus, the frequency sweeping time may be minimized if the user's application was solely the question: "Is compound X present in the sample?", since the processor and software in the spectrometer may be pre-programmed to only generate, sweep, record and analyze the terahertz frequency bands associated with the spectral signature of a particular material of concern.

Figure 3:
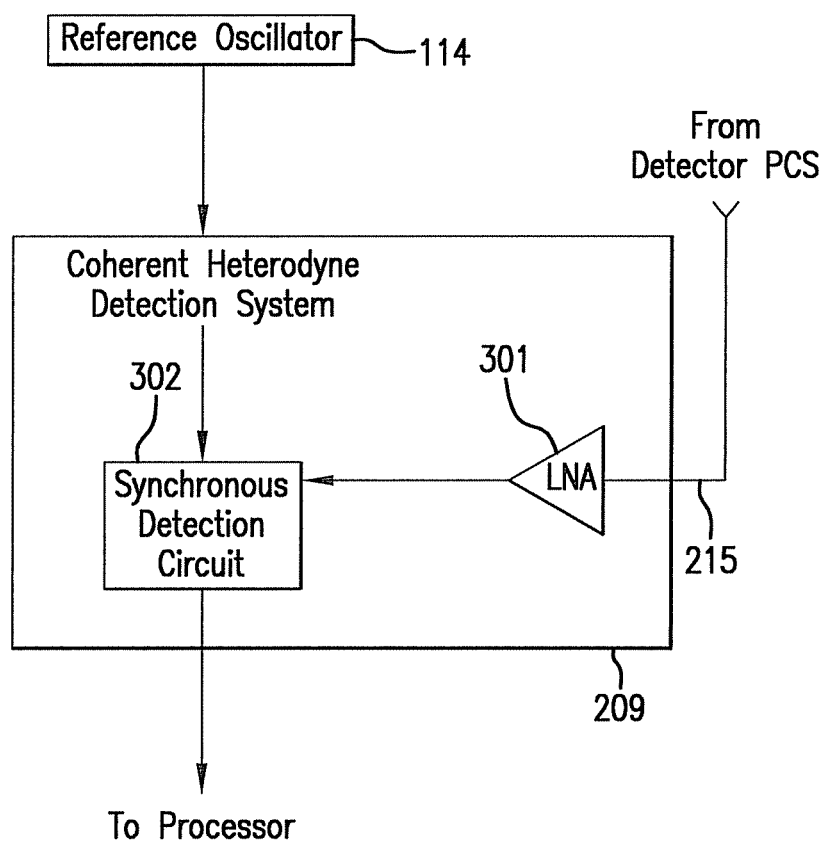
FIG. 3 is a block diagram of a heterodyne detection system subassembly.

FIG. 3 is an enlarged block diagram of a heterodyne detection system subassembly 209 shown in FIG. 2. The reference oscillator 114 provides a reference signal that may be adjusted by the operator between 0 and 10 GHz in selectable step sizes or intervals ranging from 1 Hz to 1 GHz. The signal from the detector PCS is applied on line 215 to a low noise amplifier (LNA) 301, and then to a synchronous detection circuit 302. The downconverted output of the synchronous detection circuit 302 is then forwarded to the processor 210.

In summary, certain aspects of the present disclosure may provide a compact frequency domain terahertz coherent spectrometer with either continuous tuning, or discrete tuning within certain identified frequency bands greater than 100 GHz. Such construction may employ highly compact photonic integration techniques, and room-temperature coherent THz detection. Advantageously, such devices may offer rapid identification of chemical, biological and explosive materials in both the solid-phase and the gas-phase at standard atmospheric pressure. Some embodiments may utilize a highly integrated photonic assembly employing semiconductor diode lasers employing no moving parts, so that it is inherently rugged and well-suited to field-deployable applications. The frequency-shifted optical beams are incident on the source PCS (or alternatively, in other embodiments, the detector PCS, or both), and provides a means to effect extremely high-resolution spectroscopy. Typical thermal tuning resolution and accuracy of the source lasers may perform coarse tuning over a wavelength range up to 7 nm, in intervals or step sizes of smaller than 0.0001 nm.

Of course, various modifications and improvements of the present disclosure may also be apparent to those of ordinary skill in the art. Thus, the particular combination of parts described and illustrated herein is intended to represent only certain embodiments of the present invention, and is not intended to serve as limitations of alternate devices within the spirit and scope of the invention.

It will be understood that each of the elements described above, or two or more together, also may find a useful application in other types of constructions differing from the types described above. In particular, certain configurations presented according to particular aspects of the present invention have been shown and described as discrete elements, i.e., lasers, splitters, combiners, mirrors, lenses, shifters, fiber optical cable, etc. Those skilled in the art will readily appreciate that many or all of these individual, discrete components may be fabricated and/or packaged into integrated elements. By way of particular example, the use of integrated waveguides and associated structures is envisioned for the described structures and arrangements. Alternatively, the discrete elements, i.e., lasers, splitters, combiners, mirrors, lenses, shifters, etc. may also be individually-packaged in modules with optical fiber interconnects to achieve the same topology and functionality.

While the present disclosure illustrates and describes a terahertz transceiver or spectrometer system, it is not intended to be limited to the details shown, since various modifications and structural changes may be made without departing in any way from the spirit of the present invention.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The foregoing described embodiments depict different components contained within, or connected with, different other components. It is to be understood that such depicted arrangements or architectures are merely exemplary, and that in fact many other arrangements or architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of specific structures, architectures or intermedial components. Likewise, any two components so associated can also be viewed as being "operably connected" or "operably coupled" to each other to achieve the desired functionality.

While particular embodiments of the present invention have been shown and described, it will be understood by those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," "comprise" and variations thereof, such as, "comprises" and "comprising" are to be construed in an open, inclusive sense, that is as "including, but not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Without further analysis, from the foregoing others can, by applying current knowledge, readily adapt the disclosed technology for various applications. Such adaptations should and are intended to be comprehended within the meaning and range of equivalence of the following claims.

What is claimed is:

1. A terahertz spectrometer comprising:
   first and second lasers having tunable frequencies, said first laser to produce a first output beam and said second laser to produce a second output beam, said first output beam and said second output beam having different frequencies;
   a phase modulator positioned to receive a first portion of said first output beam to controllably modulate the phase of the first output beam and producing a modulated third output beam;
   a signal source coupled to the phase modulator to allow the first output beam to be swept in phase over 360 degrees;
   a first optical element coupled to the modulated third output beam and to a portion of the second output beam to produce a composite output beam;
   a source including a first photoconductive switch activated by the composite fourth output beam to produce CW signals in a range of frequencies from 100 GHz to over 2 THz in dependence on a frequency difference between the first and second output beams;
   a radiative element coupled to the source of CW signals for causing the CW signals to be substantially simultaneously focused on or through the target;
   a second optical element coupled to a portion of the first output beam and to a portion of the second output beam to produce a composite fifth output beam;
   a detector for acquiring spectral information from said target and coupled to the composite fifth output beam, and generating, based on said spectral information and the composite fifth output beam, an electrical signal representative of a characteristic of the target,
   wherein the signal source is operable to control the phase of the CW signals for removal of an interference pattern, resulting from constructive or destructive interference between the CW signals and the composite fifth output beam on the detector as the frequency of the CW signals is swept, in the electrical signal.

2. A spectrometer as defined in claim 1, wherein the phase modulator is a lithium niobate modulator.

3. A spectrometer as defined in claim 1, wherein the frequency of signal source is selectable to allow an operator to analyze a specified frequency band of interest.

4. A spectrometer as defined in claim 1, wherein the signal source coupled to the phase modulator in swept in phase as the first output beam is swept in frequency.

5. A spectometer as defined in claim 1, further comprising a heterodyne detection system including a lock-in amplifier coupled to the detector, wherein the signal source is coupled to the lock-in amplifier.

6. A spectrometer as defined in claim 1, wherein the first and second lasers are disposed in a first housing, and the first photoconductive switch is disposed in a second housing separate from and spaced apart from the first housing, wherein the first housing and the second housing are coupled by an optical fiber.

7. A spectrometer as defined in claim 6, wherein the detector is disposed in a third housing separate from and spaced apart from the first housing, wherein the first housing and the third housing are coupled by an optical fiber.

8. A spectrometer as defined in claim 6, further comprising a power source, keypad, and display disposed in the first housing.

9. A spectrometer as defined in claim 6, further comprising a processor disposed in the first housing for determining a characteristic of the target based upon the absorption characteristics of the target in a frequency range in the 100 GHz to over 2 THz frequency band.

10. A spectrometer as defined in claim 1, wherein the detector includes a second photoconductive switch activated by the composite fifth output beam that is offset in frequency from the composite fourth output beam.

11. A spectrometer as defined in claim 10, wherein the first and second photoconductive switches are low temperature grown GaAs photoconductive switches.

12. A spectrometer as defined in claim 1, further comprising first and second thermoelectric coolers coupled to the first and second lasers, respectively, for independently coarsely tuning each of the lasers over a wavelength range of about 5 nm in intervals or step sizes of about 0.0001 nm.

13. A spectrometer as defined in claim 1, wherein the first and second lasers are DFB or DBR lasers tuned to different frequencies.

14. A spectrometer as defined in claim 1, wherein the first and second lasers are external cavity lasers.

15. A spectrometer as defined in claim 1, wherein the first optical element is a waveguide coupler.

16. A spectrometer as defined in claim 1, wherein the first photoconductive switch is biased with a constant electrical potential.

17. A method for analyzing, identifying or imaging a target, comprising:
  providing first and second lasers having first and second output beams, respectively, having different frequencies;
  phase modulating the first output beam to produce a third output beam;
  generating a CW radiative beam in the range of frequencies from 100 GHz to over 2 THz from the second and third output beams using a first photoconductive switch;
  causing the CW radiative beam to be substantially simultaneously focused on or through the target;
  combining the first output beam and the second output beam into a composite fourth output beam;
  acquiring a spectral information signal from said target using a second photoconductive switch activated by said composite fourth output beam;
  sweeping the frequency of the CW radiative beam over a selected range of frequencies;
  generating an electrical signal representative of a characteristic of said target using the spectral information signal acquired during the sweeping of the CW radiative beam over the selected range of frequencies; and
  controllably adjusting the phase modulation of the first output beam so as to modify an interference pattern over the selected range of frequencies of the CW radiative beam.

\* \* \* \* \*